US008435744B2

(12) United States Patent
Verdier et al.

(10) Patent No.: US 8,435,744 B2
(45) Date of Patent: May 7, 2013

(54) METHOD USEFUL FOR DETECTING ENCEPHALOPATHIES

(75) Inventors: Jean-Michel Verdier, Saint-Gely-du Fesc (FR); Catherine Gregoire, Berre l'Etang (FR); Veronique Perrier-Rondard, Jacou (FR)

(73) Assignees: Institut National de la Sante et de la Recherche Medicale, Paris (FR); Centre National de la Recherche Scientifique, Paris (FR)

( * ) Notice: Subject to any disclaimer, the term of this patent is extended or adjusted under 35 U.S.C. 154(b) by 1306 days.

(21) Appl. No.: 11/921,640

(22) PCT Filed: Jun. 7, 2006

(86) PCT No.: PCT/FR2006/050528
§ 371 (c)(1),
(2), (4) Date: Mar. 3, 2008

(87) PCT Pub. No.: WO2006/131676
PCT Pub. Date: Dec. 14, 2006

(65) Prior Publication Data

US 2009/0130689 A1 May 21, 2009

(30) Foreign Application Priority Data

Jun. 7, 2005 (EP) .................................... 05300463

(51) Int. Cl.
*G01N 33/53* (2006.01)
*C07K 1/13* (2006.01)

(52) U.S. Cl.
USPC ........................................... 435/7.1; 530/402

(58) Field of Classification Search ........................ None
See application file for complete search history.

(56) References Cited

U.S. PATENT DOCUMENTS

| | | | | |
|---|---|---|---|---|
| 5,142,033 | A | 8/1992 | Innis | |
| 2002/0012639 | A1 | 1/2002 | Glenn, Jr. et al. | |
| 2005/0049487 | A1 | 3/2005 | Johnson et al. | |
| 2005/0064505 | A1 | 3/2005 | Soto-Jara et al. | |
| 2005/0171103 | A1 | 8/2005 | Stokes et al. | |
| 2009/0130689 | A1* | 5/2009 | Verdier et al. | 435/7.1 |

FOREIGN PATENT DOCUMENTS

| | | | |
|---|---|---|---|
| WO | WO 01/35104 | A1 | 5/2001 |
| WO | WO 02/04954 | A2 | 1/2002 |
| WO | WO 03/087057 | * | 10/2003 |
| WO | WO 03/087057 | A1 | 10/2003 |
| WO | WO 03/094904 | A1 | 11/2003 |
| WO | WO 2005/033102 | * | 4/2005 |
| WO | WO 2005/033102 | A2 | 4/2005 |

OTHER PUBLICATIONS

Etessami et al. (Biochemical and Biopphysical Research Communications). 2005; 330 (1): 5-10.*
Saborio et al. Nature. Jun. 14, 2001;411 (6839): 810-813.*
Rodriquez-Spong et al. (Advanced Drug Delivery Reviews. 2004; 56: 241-274).*
Ayrolles-Torro et al. (Journal of Neuroscience. Oct. 2011; 31(4): 14882-14892).*
Dan Serban et al., "Rapid Detection of Creutzfeldt-Jakob Disease and Scrapie Prion Proteins," Neurology, vol. 40, No. 1, pp. 110-117, Jan. 1990.
Surachai Supattapone et al., "Elimination of Prions by Branched Polyamines and Implications for Therapeutics," Proc. Natl. Acad. Sci., vol. 96, No. 25, pp. 14529-14534, Dec. 7, 1999.
Winslow S. Caughey et al., "Inhibitions of Protease-resistant Prion Protein Formation by Porphyrins and Phthalocyanines," Proc. Natl. Acad. Sci. USA, vol. 95, pp. 12117-12122, Oct. 1998.
Carsten Korth et al., "Acridine and Phenothiazine Derivatives as Pharmacotherapeutics for Prion Disease," Proc. Natl. Acad. Sci., vol. 98, No. 17, pp. 9836-9841, Aug. 14, 2001.
Cai'ne Wong et al., "Sulfated Glycans and Elevated Temperature Stimulate $PrP^{Sc}$-Dependent Cell-Free Formation of Protease-Resistant Prion Protein," The EMBO Journal, vol. 20, No. 3, pp. 377-386, 2001.
Reza Etessami et al., "Scratch-Wounding Renders Cultivated Cells Less Permissive to Prion Infection," Biochemical and Biophysical Research Communications, vol. 330. pp. 5-10, 2005.
Veronique Perrier et al., "Mimicking Dominant Negative Inhibition of Prion Replication Through Structure-Based Drug Design," Proc. Natl. Acad. Sci., vol. 97, No. 11, pp. 6073-6078, May 23, 2000.
Remi Demaimay et al., "Pharmacological Studies of a New Derivative of Amphotericin B, MS-8209, in Mouse and Hamster Scrapie," Journal of General Virology, vol. 75, pp. 2499-2503, 1994.
Katsumi Doh-Ura et al., "Lysosomotropic Agents and Cysteine Protease Inhibitors Inhibit Scrapie-Associated Prion Protein Accumulation," Journal of Virology, vol. 74, No. 10, pp. 4894-4897, May 2000.
Noriyuki Nishida et al., "Successful Transmission of Three Mouse-Adapted Scrapie Strains to Murine Neuroblastoma Cell Lines Overexpressing Wild-Type Mouse Prion Protein," Journal of Virology, vol. 74, No. 1, pp. 320-325, Jan. 2000.
Kai-Uwe D. Grathwohl et al., "Sensitive Enzyme-Linked Immunosorbent Assay for Detection of $PrP^{Sc}$ In Crude Tissue Extracts From Scrapie-Affected Mice," Journal of Virological Methods, vol. 64, pp. 205-216, 1997.
Suzette A. Priola et al., "Porphyrin and Phthalocyanine Antiscrapie Compounds," Science, vol. 287, No. 5457, pp. 1503-1506 Feb. 25, 2000.
Bruno Oesch et al., "Properties of the Scrapie Prion Protein: Quantitative Analysis of Protease Resistance," Biochemistry, vol. 33, pp. 5926-5931, 1994.
Jiri Safar et al., "Eight Prion Strains Have $PrP^{Sc}$ Molecules with Different Conformations," Nature Medicine, vol. 4, No. 10, pp. 1157-1165, Oct. 1998.
O. Schaller et al., "Validation of a Western Immunoblotting Procedure for Bovine $PrP^{Sc}$ Detection and its Use as a Rapid Surveillance Method for the Diagnosis of Bovine Spongiform Encephalopathy (BSE)," Acta Neuropathol., vol. 98, pp. 437-443, 1999.
Stanley B. Prusiner et al., "Purification and Structural Studies of a Major Scrapie Prion Protein," Cell, vol. 38, pp. 127-134, Aug. 1984.

* cited by examiner

*Primary Examiner* — Shanon A Foley
(74) *Attorney, Agent, or Firm* — Oliff & Berridge, PLC

(57) ABSTRACT

The invention concerns a method of detecting a TSSE Disease or prion disease. The invention further concerns a method for amplifying oligomerization of isoforms of the cellular prion $PrP^{Sc}$.

5 Claims, 3 Drawing Sheets

METHOD USEFUL FOR DETECTING ENCEPHALOPATHIES

Figure 1:
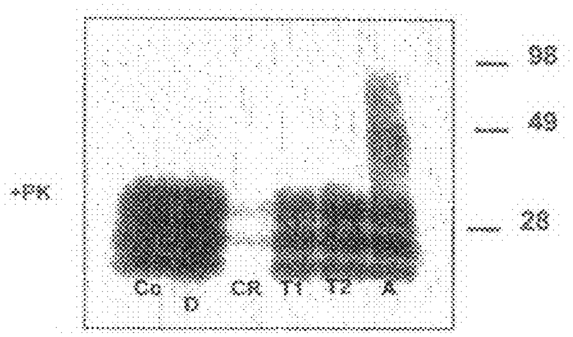

The present invention relates principally to a method useful for amplifying the oligomerization and/or the infectious titer of $PrP^{SC}$ isoforms of the cellular prion protein $PrP^{C}$. It also relates to the use of such a method for the diagnosis, characterization, clinical monitoring, etc., of encephalopathy, in particular of transmissible subacute spongiform encephalopathies (TSSEs) including bovine spongiform encephalopathies (BSEs).

Prion diseases or transmissible subacute spongiform encephalopathies (TSSEs) are fatal neurodegenerative conditions which affect both humans and animals. TSSEs include essentially Creutzfeldt-Jakob disease, in humans (CJD), scrapie in sheep and goat and bovine spongiform encephalopathy (BSE) in cattle. Other encephalopathies have been demonstrated in felines, in mink or in certain wild animals, such as deer or moose.

The infectious agent responsible for these diseases is unconventional. Currently, the dominating hypothesis is that of "prions", according to which the cellular prion protein, $PrP^{C}$, synthesized by the host organism, would be capable of adopting a pathological conformation, called $PrP^{Sc}$, which denotes the "scrapie" isoform.

These two isoforms have the same amino acid sequence but differ in terms of their secondary structure: $PrP^{SC}$ has a significantly higher content of beta-pleated sheets, whereas normal PrP ($PrP^{C}$) has a greater number of alpha helices.

Two biochemical properties generally make it possible to distinguish these two isoforms:

- $PrP^{Sc}$ is partially resistant to proteases, in particular to proteinase K (PK), which produces a cleavage of its N-terminal end. After the action of PK, $PrP^{Sc}$ is commonly referred to as PrP27-30 because of the apparent molecular weight of the diglycosylated form: it is generally accepted that the $PrP^{Sc}$ cleavage site is located between amino acids 89 and 90 (Prusiner S. B. et al., Cell, (1984), 38, 127-134) for the usual strains,
- $PrP^{Sc}$ is insoluble in nonionic detergents, such as Triton X100 or Triton 114.

The normal form of the prion protein ($PrP^{C}$) is, in principle, completely degraded by proteases and entirely soluble in the presence of nonionic detergents.

The accumulation of $PrP^{Sc}$ in the brain of individuals or animals suffering from TSSE causes degeneration of said brain. Research on these diseases has shown a remarkable increase in development since the mad cow crisis in Europe and the appearance of the new variant of Creutzfeldt-Jacob disease in humans (vCJD). Progress has, as a result, been made in terms of the knowledge of these unconventional infectious agents. However, at the current time, no available treatment exists for treating patients suffering from CJD, nor is there a test for early diagnosis.

Over the last decade, several molecules having an "anti-prion" activity and an innovative chemical structure have been identified, such as (i) dendrimers (Supattapone S. et al., Proc. Natl. Acad. Sci. U.S.A. (1999) 96, 14529-34); (ii) derivatives of porphyrins and phthalocyanins (Caughey W. S. et al., Proc. Natl. Acad. Sci. U.S.A. (1998) 21, 12117-22); (iii) derivatives of quinacrine and of chlorpromazine (Doh-Ura et al., J Virol (2000) 74, 4894-7), (Korth C et al., Proc. Natl. Acad. Sci. U.S.A. (2001) 98, 9836-41). These drugs are capable of partially or completely eliminating the infectiousness of chronically prion-infected ScN2a mouse neuroblastomas. However, their action is very limited in vivo (Demaimay R et al., J Gen. Virol (1994) 75, 2499-503; Priola S A et al., Science (2000)287, 1503-6). The reasons explaining the lack of effectiveness of these products in vivo are probably their lack of specificity with respect to the infectious agent, since the mechanism of action of these drugs is poorly or not at all known, and the difficulty that these products have in crossing the blood-brain barrier.

Drug-screening studies carried out in order to identify "anti-prion" products have also led to the identification of two compounds, i.e. 2-amino-6-[(2-aminophenyl)thio]-4-(2-furyl)pyridine-3,5-dicarbonitrile and N'-1-({5-[(4,5-dichloro-1H-imidazol-1-yl)methyl]-2-furyl}carbonyl)-4-methoxybenzene-1-sulfonohydrazide, which exhibit an inhibitory activity in cell culture (Perrier V. et al., Proc. Natl. Acad. Sc. U.S.A. (2000) 97, 6073-6078). However, the $IC_{50}$ values (concentration for which 50% of the $PrP^{Sc}$ content in the cells is inhibited) obtained for these products, which is of the order of 15 μM, is not found to be compatible with an application in vivo. Moreover, Etessami et al. (Biochem. Biophys. Res. Comm., 2005, 330:5) have also observed that the release of nucleotides into the extracellular medium of damaged cells is susceptible of reducing de novo infection by the prion.

In diagnostic terms, the most recent methods are based on a selected detection of abnormal PrP ($PrP^{Sc}$), associated with the infectious agent, by taking advantage of its partial protease resistance.

In this respect, it is possible to distinguish:

- Western blotting methods, which are based on the immunodetection of $PrP^{Sc}$ in a tissue extract, after treatment of the extract with a protease so as to destroy the normal $PrP^{C}$ isoform, separation of the proteins from the extract by electrophoresis, transfer onto a polymer membrane, and detection with a specific antibody which recognizes PrP (Schaller O. et al., Acta Neuropathol., 1999, 98, 437-443), and
- ELISA assays, which also involve treatment of the tissue extracts with a protease.

Among these various tests, which involve a treatment of the tissue extracts with a protease, mention may be made of:

- that described by Serban et al. (Neurology, 1990, 40, 100), who developed a test for detecting $PrP^{Sc}$ which includes the immobilization of the proteins on a nitrocellulose membrane, followed by protease digestion, denaturation, and immunodetection with monoclonal antibodies,
- that described by Oesch et al. (Biochemistry, 1994, 33, 5926-5931), who proposed, in order to quantify the amount of $PrP^{Sc}$, an immunofiltration assay for the purification of $PrP^{Sc}$ (ELIFA or enzyme-linked immunofiltration assay),
- that described by Gratwohl K. U. et al., J. Virol. Methods, 1997, 64, 205-216, who proposed an ELISA assay. After treatment of the samples with proteinase K and purification of $PrP^{Sc}$ by centrifugation, the latter is adsorbed onto microtitration plates and detected using rabbit polyclonal antibodies,
- that described by Safar J. et al., Nature Med., 1998, 10, 1157-1165, who do not use proteinase K and compare the immunoreactivity of $PrP^{Sc}$ immobilized on a solid support, according to whether or not it has been subjected beforehand to a denaturing treatment.

More recently, document WO 01/35104 has proposed a test involving, successively, the treatment of a sample presumed to contain $PrP^{Sc}$ with proteinase K under conditions adjusted so as to allow complete degradation of the $PrP^{C}$ protein while at the same time conserving all or part of the repeated octapeptide motifs of the $PrP^{Sc}$ protein, the subsequent bringing of said sample thus treated into contact with a ligand, in particular an antibody specific for the octapeptide motifs, and the possible detection of a repeated octapeptide motifs-ligand complex.

WO 02/04954 describes a method for detecting prion using a step for amplifying the $PrP^{Sc}$ protein by bringing abnormal PrP into contact with a known amount of normal PrP.

In general, these various tests have the drawback of lacking sensitivity and, consequently, producing false negatives. Furthermore, they are carried out post-mortem.

In fact, the early detection of prions in the blood or urine would require a test 10 to 100 times more sensitive than those which currently exist. In addition, the specificity with respect to the abnormal isoform, $PrP^{Sc}$, is an essential condition for the development of an effective test.

Consequently, there remains a need for novel methods for detecting encephalopathies, in particular methods which can be applied in living beings, which are rapid and which make it possible to detect the pathology at a very early stage.

An object of the present invention is precisely to propose a novel method of diagnosis for encephalopathies, which makes it possible to establish an early diagnosis of the disease, i.e. ante-mortem, in humans or animals, and which is noninvasive.

According to one of its aspects, the present invention is principally directed toward a method useful for selectively amplifying the oligomerization and/or increasing the infectious rate of at least one $PrP^{Sc}$ isoform of the PrP cellular prion protein, where appropriate in a mixture with the $PrP^{C}$ isoform, characterized in that it comprises bringing said $PrP^{Sc}$ isoform, under conditions suitable for amplification, together with an effective amount of at least one compound of general formula I

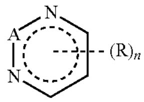
(I)

in which A, R and n are as defined hereinafter.

According to another of its aspects, the present invention is directed toward a method useful for detecting a $PrP^{Sc}$ isoform of the $PrP^{C}$ cellular prion protein, comprising at least the implementation of a method as defined above and a step of detection of said isoform. This detection step can be carried out by a screening method, for example of the hybridization or antibody/antigen interaction type.

According to another of its aspects, the present invention relates to a method useful for detecting the presence or the risk of the occurrence of an encephalopathy in an animal or human individual, said method comprising at least:

- bringing a biological sample from said individual together with an effective amount of at least one compound of general formula I as defined above, under conditions suitable for the amplification of the oligomerization of $PrP^{Sc}$ isoform(s) possibly present in said sample, and
- detecting the possible presence of said $PrP^{Sc}$ isoform, indicative of the presence or of the risk of development of an encephalopathy in said individual.

The method according to the invention is particularly useful for detecting a transmissible subacute spongiform encephalopathy (TSSE), and especially a Creutzfeldt-Jakob disease in humans, scrapie in sheep and goat, and bovine spongiform encephalopathy.

According to a specific embodiment, the compound of general formula I can be used in a form associated with a marker suitable for luminescent detection or detection by affinity.

According to another specific embodiment of the invention, the detection step involves an immuno-detection process, in particular using specific antibodies.

According to this second variant, this detection comprises at least the treatment of all or part of said sample with a protease, such as, for example, protease K, so as to destroy the normal PrP isoform, the separation of the proteins and the detection of the $PrP^{Sc}$ isoform possibly present, in particular using a specific antibody. The step of destruction of the normal PrP isoform is generally carried out after the step of the $PrP^{Sc}$ isoform oligomerization amplification.

A mixture of antibodies SAF60 and SAF69, specific for the sequences 157-161 of human PrP, and SAF70, specific for the sequence 156-162 of human PrP, is in particular suitable for the detection.

Similarly, the treatment with proteinase K can be carried out under the conditions described in document WO 01/35104, which result in complete degradation of the $PrP^{C}$ protein while at the same time conserving all or part of the repeated octapeptide motifs of the $PrP^{Sc}$ protein. In this case, the detection can be carried out by subsequently bringing said sample thus treated into contact with a ligand, in particular octapeptide motifs, for detecting the possible presence of repeated octapeptide motifs-ligand complex(es).

According to yet another of its aspects, the present invention relates to a kit for selectively amplifying the oligomerization of at least one $PrP^{Sc}$ isoform and also to a kit useful for diagnosing TSSEs, comprising, as a reagent, at least one compound of general formula I.

Unexpectedly, the inventors have observed that the compounds of general formula I prove to be particularly effective for selectively amplifying the oligomerization of the $PrP^{Sc}$ isoforms of the cellular prion protein, in particular in the presence of the nonpathogenic form thereof. Thus, the compounds of general formula I have the particularity of increasing the presence of oligomeric forms of $PrP^{Sc}$ without increasing those of the normal $PrP^{C}$ isoform. Quite obviously, the compounds in accordance with the invention act specifically on the $PrP^{Sc}$ molecules.

This ability is particularly advantageous insofar as it makes it possible to diagnose at an early stage the risk of the occurrence of an encephalopathy.

By selectively amplifying, in a biological sample, $PrP^{Sc}$ isoforms that are not detectable, as such, with conventional diagnosis methods, detection at a significantly earlier stage is from now on made possible.

For obvious reasons, such an early diagnosis can only be beneficial in curative and economic terms, and constitute a major need in terms of public health and with respect to sanitary safety.

Thus, the invention makes it possible to develop a test for detecting prions in a physiological fluid, such as urine and blood, for the preclinical diagnosis of scrapie in sheep and of bovine spongiform encephalopathy, and thus to detect sick animals which can currently pass into the food chain.

In addition, the methods according to the invention applied to blood samples give a better guarantee with regard to human blood transfusions and make it possible to establish a test for the early diagnosis of TSSEs in humans, or even the optimization of future treatments.

As specified above, the invention is based on the use of the compound of general formula I as follows:

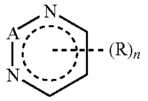

(I)

in which:

A represents a $-C(H)_xR_1-$, $-CO-$, $C(H)_xO(R_1)$, $-C(H)_xS(R_1)-$, $-CN(R_1)(R_2)-$ group with x being equal to 0 or 1, and $R_1$ and $R_2$ representing, independently of one another, a hydrogen atom, a saturated or unsaturated, linear, branched or cyclic, $C_1$ to $C_6$ alkyl radical, where appropriate substituted, the symbol

means that the pyrimidyl ring may be saturated, unsaturated or aromatic,

R represents a radical chosen from:

a hydrogen atom, an $OR'_1$, $N(R'_1)(R'_2)$, $SR'_1$ group with $R'_1$ and $R'_2$ representing, independently of one another, a group as defined above for $R_1$ and/or $R_2$, a saturated or unsaturated, linear, branched or cyclic, $C_1$ to $C_{10}$ hydrocarbon-based radical, the hydrocarbon-based chain of which may, where appropriate, be interrupted with one or more heteroatoms chosen from S, O and N atoms, and where appropriate, substituted, n is equal to zero or is an integer ranging from 1 to 3, and salts, solvates, isomers or derivatives thereof.

According to one embodiment, when a radical R is present on a nitrogen atom of the pyrimidyl ring, it is a hydrogen atom.

As regards the salts thereof, they may be any of the inorganic or organic salts insofar as they are found to be compatible with the implementation of the invention.

As regards the derivatives thereof, they may more particularly be, for the purpose of the invention, compounds of general formula I incorporating into their structure at least one entity, which may or may not belong to a labeling system, capable of providing them with a method of detection, for example luminescent detection, like for example a signal that is visible in the infrared range or by fluorescence, for instance Europium, or detection by affinity, such as biotin labeling in the case of streptavidin/biotin recognition.

The entity, which is generally chemical, intended to provide the compound of general formula I with a method of labeling for detection, can be attached to the molecule of general formula I by conventional methods.

Of course, its location is selected so as not to affect the expected reactivity of the derivative of general formula I thus obtained.

More particularly, the pyrimidyl ring is an aromatic ring.

According to one embodiment, when the pyrimidyl ring is an aromatic ring, R is in the meta- or para-position with respect to the group A.

According to a specific embodiment, n is equal to 1.

As regards A, it is more particularly a $-CS(R_1)-$ motif with $R_1$ representing an alkyl radical as defined above.

R preferably represents an unsaturated or aromatic $C_5$ to $C_6$ heterocyclic radical incorporating one or two heteroatoms chosen from S, N and O atoms.

It is more particularly a thienyl radical, where appropriate substituted.

As possible substituents, mention may more particularly be made of halogen atoms especially chosen from fluorine, bromine, iodine and chlorine atoms, and more particularly bromine; OH, OR', NR'R", SR' and R' radical with R' and R" representing, independently of one another, a linear or branched $C_1$ to $C_{10}$ alkyl radical; saturated, unsaturated or aromatic $C_4$ to $C_8$, in particular $C_5$ to $C_6$, heterocyclic radicals, optionally substituted, comprising one or more heteroatoms chosen from N, O and S, for example a thienyl radical, a thiophenyl radical or a thiazolyl radical.

According to a specific embodiment, a substituent may advantageously be chosen from a bromine or a thienyl radical.

By way of nonlimiting representation of the compounds of general formula I, mention may more particularly be made of 4-(5-bromo-2-thienyl)-2-(methylthio)pyrimidine having the formula as follows:

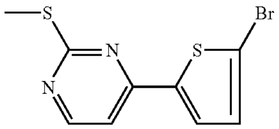

and 4-(5-thienyl-2-thienyl)-2-(amino)pyrimidine having the formula as follows:

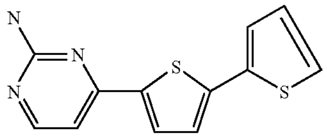 [SMILES: Nc1nccc(-c2ccc(-c3cccs3)s2)n1]

and salts or derivatives thereof.

Given their reactivity with respect to the $PrP^{Sc}$ isoforms, the compounds of general formula I manifestly have the ability to bind to at least one amino acid.

Without wishing to be bound to any theory, it would appear that the compounds in accordance with the present invention are found to be capable of binding to at least one of the following two regions of the C-terminal part of the PrP protein:

a region located at the disulfide bridge (residues Cys 179 and Cys 214) which connects the H2 and H3 helices, a region located in the H1 helix (comprising residues 144-154), located at the interface of the PrP dimer in the crystalline structure.

The amplification is generally carried out by incubation of the cells presumed to be infected or not, with an effective amount of compound(s) of general formula I. This incubation is carried out under conditions suitable for the amplification, generally at 37° C., at a physiological pH, for a sufficient period, which may be up to approximately 3 days.

For the purpose of the present invention, the term "effective amount" means at least the minimum and sufficient amount to observe amplification of the oligomerization of at least one $PrP^{Sc}$ isoform possibly present in the biological sample which is the subject of the analysis.

For obvious reasons, this amount can vary significantly depending on the desired sensitivity in terms of the diagnostic method and/or the amount of $PrP^{Sc}$ isoform(s) initially present.

For example, this concentration can range from 0.1 to 20 μM.

In the case of a method for the immunodetection of $PrP^{Sc}$ isoforms, the latter can be carried out by conventional screening methods such as hybridization or antibody/antigen reaction. Such a treatment requires prior cell lysis using conventional physical, mechanical or chemical methods.

According to a variant of the invention, the cell lysates having undergone the amplification method according to the invention may, prior to the detection of the $PrP^{Sc}$ isoforms, be subjected to a partial digestion with a protease, and in particular protease K, so as to eliminate the $PrP^{C}$ molecules and therefore to conserve only the $PrP^{Sc}$ isoforms in the biological sample. The presence of these $PrP^{Sc}$ isoforms can subsequently be detected by simple conventional analysis, in particular of immunoblotting type.

For example, said PK treatment can be carried out in the following way: 1 μg of PK per 50 or 25 μg of proteins to be digested for 1 h at 37° C. for a total of 200 μg of proteins in a final volume of 400 μl.

According to a specific embodiment of the invention, this treatment with protease K can also be carried out under the conditions described in document WO 01/35104, the content of which is incorporated into the present application by way of reference. This treatment aims at completely degrading the normal $PrP^{C}$ isoform while at the same time conserving all or part of the repeated octapeptide motifs of $PrP^{Sc}$, irrespective of the strain of unconventional transmissible agent (UTA).

It should be noted that a certain number of parameters are tightly linked to one another: the concentration of proteinase K depends directly on the duration of the treatment (incubation time) of the sample: it may thus be considered that, at 37° C. for example, a 10 minutes incubation with a PK at a concentration of between 30 and 200 μg/ml of homogenate at 10% is equivalent to a 30 minutes incubation with a PK at a concentration of between 10 μg/ml and 70 μg/ml of homogenate at 10%. For example, a 30 minutes incubation with a PK at 25 μg/ml is equivalent to a 10 minutes incubation with a PK at a concentration of 75 μg/ml.

In the case of the use of a derivative of a compound of general formula I, i.e. provided with a labeling method, the detection can be carried out according to the standard conditions recommended for the marker selected.

A subject of the present invention is also a diagnostic kit useful for implementing a method in accordance with the invention, characterized in that it comprises, as a reagent, at least one compound of general formula I.

According to another of its aspects, the present invention relates to a kit for diagnosing a TSSE, characterized in that it comprises at least one compound of general formula I in combination with a ligand for the PrP cellular protein, and in particular for a $PrP^{C}$ isoform. More particularly, it is an antibody which may or may not be monoclonal, or a mixture of monoclonal antibodies.

Such antibodies are in particular described in Nishida et al. (J. Virol, 74:320-325, 2000) and sold by the company Spibio. They are also described in patent WO 01/35104.

According to another of its aspects, the present invention relates to a kit useful for diagnosing a TSSE, characterized in that it comprises at least one compound of general formula I in the form of a derivative provided with a labeling system. The labeling may be suitable for luminescent detection, in particular by fluorescence, or by affinity, such as a streptavidin/biotin couple, for example.

The examples and figures which appear hereinafter are given by way of nonlimiting illustration of the field of the invention:

FIGURES

FIG. 1: It illustrates the activity of a compound A in accordance with the invention, on the $PrP^{Sc}$ from infected N2a58/22L cells. The analysis is carried out by immunoblotting after treatment with proteinase K (Co=cells having undergone no treatment, D=cells treated with the solvent alone (DMSO), CR=Congo Red, T1 and T2 are two ineffective control compounds.

Figure 2:
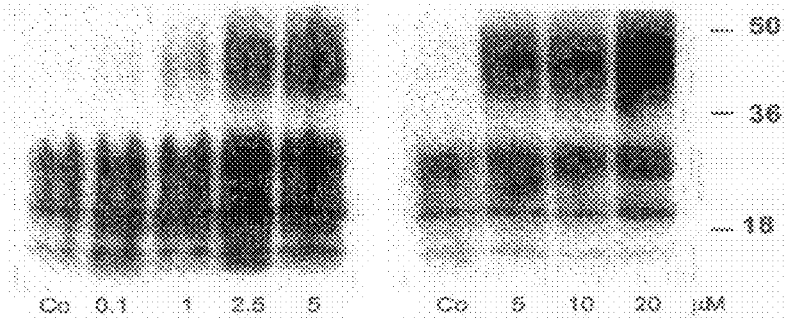

FIG. 2: It illustrates the dose-response activity of the compound A in accordance with the invention, on the $PrP^{Sc}$ from infected N2a58/22L cells. The analysis is carried out by immunoblotting after treatment with proteinase K. The compound A was tested using a range of concentrations from 0.1 to 20 μM, in order to establish a dose-response curve (Co=cells having undergone no treatment, the figures from 0.1 to 20 correspond to the product concentrations used (in μM)).

Figure 3:
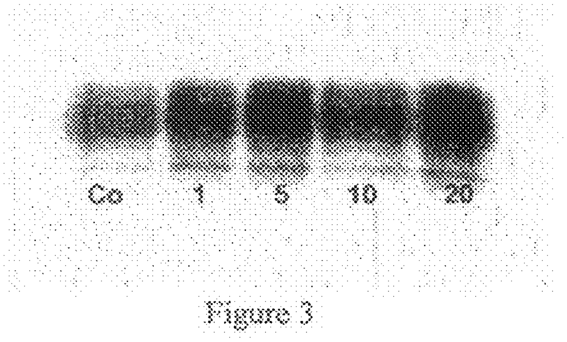

FIG. 3: It reports the effect of the compound A according to the invention on the $PrP^{C}$ from uninfected N2a58 cells. The analysis is carried out by immunoblotting (the figures 1 to 10 μM correspond to the concentrations of product A used during the incubation with the cells).

Figure 4:
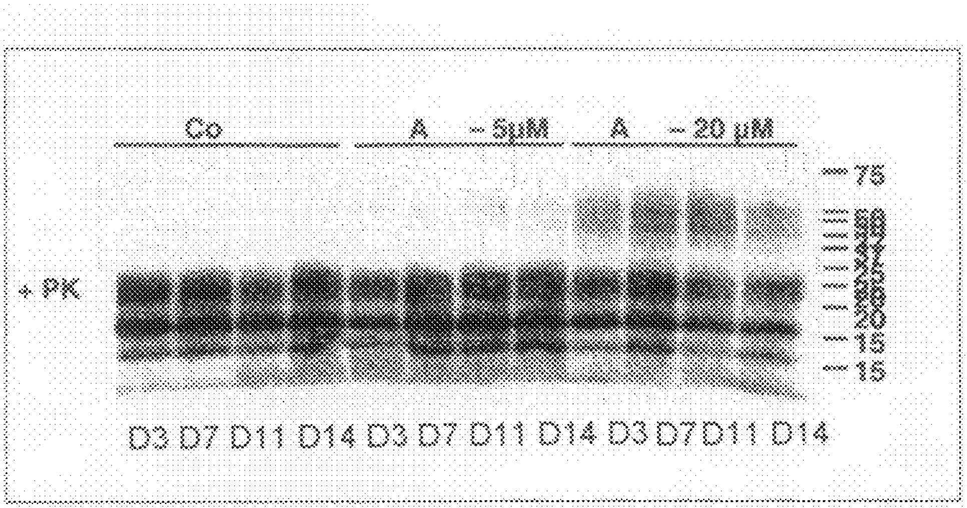

FIG. 4: It illustrates the dose-response activity of the compound A on the $PrP^{Sc}$ from infected N2a58/22L cells. The analysis is carried out by immunoblotting after treatment with proteinase K. The compound A was tested using a range of concentrations of 5 or 20 μM for 3 to 14 days (Co=cells having undergone no treatment, the figures 5 and 20 correspond to the product concentrations used (in μM)).

Figure 5:
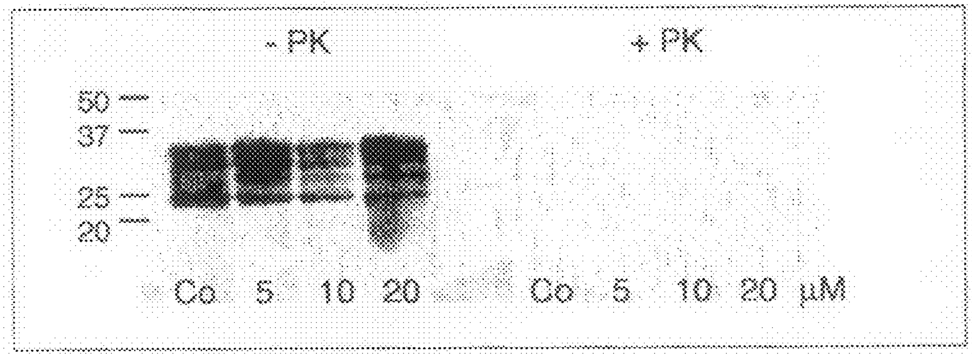

FIG. 5: It reports the absence of effect of the compound A on the $PrP^{C}$ from uninfected N2a58 cells. The analysis is carried out by immunoblotting before and after treatment with proteinase K. The figures 5 to 20 μM correspond to the concentrations of compound A used during the incubation with the cells.

Figure 6:
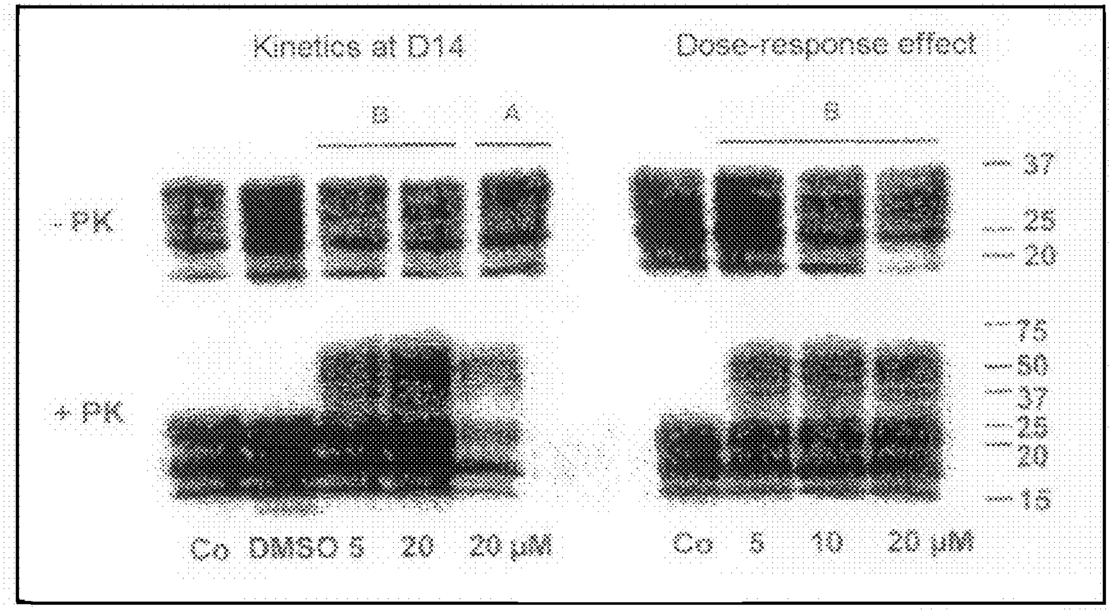

FIG. 6: It illustrates a comparison between the effect of the compound A at 5 and 20 μM and that of a compound B in accordance with the invention at 20 μM on the $PrP^{Sc}$ from infected N2a58/22L cells after prolonged incubation of the compounds for 14 days. The samples were analyzed before and after treatment with proteinase K (Co=cells having undergone no treatment, the figures 5 and 20 correspond to the product concentrations used (in μM)).

The assays were carried out using, as a compound of general formula I, either the compound A, i.e. 4-(5-bromo-2-thienyl)-2-(methylthio)pyrimidine sold by the company Maybridge under the reference ACD 30432, or the compound B, i.e. 4-(5-thienyl-2-thienyl)-2-(amino)-pyrimidine sold by the company Maybridge under the reference SEW 02312.

EXAMPLE 1

In vitro Screening on Cell Cultures Chronically Infected with Prions

The compound A is tested in vitro on murine neuroblastoma lines chronically infected with the 22L prion strain (scrapie strain stabilized in mice) (Nishida N. et al., J. Virol. (2000) 74, 320-325). This infected cell line, called N2a/22L, produces a large amount of $PrP^{Sc}$ molecules which are resistant to partial digestion with proteinase K and which have properties reminiscent of those of prions. The infected N2a/22L cells are capable of causing a TSSE when they are inoculated intracerebrally into mice. The infected N2a/22L cells are incubated with the compound A, at a concentration of 20 μM, for a period of 3 days at 37° C. and 5% $CO_2$.

After 3 days, the confluent cells are lyzed in the presence of detergents. The cell lysates, normalized with respect to their amount of proteins, are subjected to partial digestion with proteinase K (PK) in order to eliminate the $PrP^C$ molecules compared with the untreated control cells. The product is tested in duplicate in order to eliminate nonreproducible effects.

In a second step, the compound A was retested using a range of concentrations from 0.1 to 20 μM, in order to determine whether a dose-response effect could be obtained. An approximately 90-fold increase in the signal is observed at 20 μM on the oligomeric forms compared with an untreated control.

FIGS. 1 and 2 report the results obtained by immunoblotting analysis, after proteinase K treatment. It is observed that the compound A notably increases the amount of $PrP^{Sc}$ in the infected cells.

Since the infected cells express both $PrP^C$ molecules and $PrP^{Sc}$ molecules, the question of which of these two isoforms the compound A acted upon was investigated. In particular, the question of whether the oligomers which migrate at 49 kDa and 98 kDa (FIG. 1) were $PrP^C$ oligomers that had become more resistant to proteinase K subsequent to their interaction with the compound A was investigated. For this, uninfected cells which express only the $PrP^C$ isoform were incubated in the presence of the compound A. The results given in FIG. 3 show that the compound A does not increase the oligomerization of $PrP^C$ in the cells.

EXAMPLE 2

Effect of the Compound A on Uninfected or Prion-Infected Cell Cultures

The compound A was incubated in the presence of the N2a58/22L cells for a period of 14 days, at a concentration of 5 and 20 μM.

Cell lysates were analyzed by immunoblotting after a period of 3, 7, 11 and 14 days.

The results indicate that prolonged incubation of this compound on the infected cells does not induce the appearance of oligomeric forms having a size greater than those observed over a period of 3 days. No depletion of the monomeric form $PrP^{Sc27-30}$ to the benefit of a greater amplification of the oligomeric forms around 50-60 kDa was observed either (FIG. 4).

On the other hand, at the concentration of 20 μM of compound A, the proportion of amplified oligomeric forms is equivalent at 3 days as it is at 14 days, which shows that the state of equilibrium is reached in 3 days, which is not the case for the concentration of 5 μM, where the equilibrium is reached after 11 days.

The effect of the compound A on the induction of the appearance of the proteinase K-resistant form in the protein of the normal $PrP^C$ prion was studied.

Normal N2a58 cells, derived from the same line as the infected N2a58/22L cells, were incubated in the presence of compound A for a period of 3 days. The immunoblotting analysis of the samples before and after proteinase K digestion does not make it possible to demonstrate oligomeric forms of the normal prion protein, PrP nor the appearance of bands resistant to proteinase K digestion (FIG. 5).

These results suggest that the compound A acts specifically on the amplification of the infectious isoform $PrP^{Sc}$ of the prion protein.

EXAMPLE 3

Effect of the Compound B on Uninfected or Prion-Infected Cell Cultures

The dose-response curve for the compound B was obtained on N2a58/22L cells incubated for 3 days with concentrations of B from 5 to 20 μM. At 5 μM, the amount of oligomeric forms of $PrP^{Sc}$ is identical to that observed for the concentration of 10 or 20 μM, which suggests that, at 5 μM, the dose-response curve already reaches its plateau.

Moreover, comparative kinetics between the compounds B and A, over an incubation period of 14 days, reveal that compound B has a greater amplification capacity.

After incubation of the cells for 14 days with the product B, at a concentration of 20 μM, the amount of oligomeric forms observed is much greater than for the compound A under the same conditions.

All these results are illustrated in FIG. 6.

The invention claimed is:

1. A method for selectively amplifying the oligomerization of at least one $PrP^{Sc}$ isoform of the $PrP^C$ cellular prion protein, the method comprising bringing said $PrP^{Sc}$ isoform, under conditions suitable for amplification, together with an effective amount of at least one compound

selected from the group consisting of 4-(5-bromo-2-thienyl)-2-(methylthio)pyrimidine, 4-(5-thienyl-2-thienyl)-2-(amino) pyrimidine, and salts thereof.

2. The method as claimed in claim 1, wherein the amplification is carried out in the presence of the $PrP^C$ isoform.

3. The method as claimed claim 1, wherein said compound is attached to at least one entity capable of providing it with a method of detection.

4. The method as claimed in claim 3, wherein said entity is a marker suitable for luminescent detection or detection by affinity.

5. A method useful for detecting a $PrP^{Sc}$ isoform of the $PrP^C$ cellular prion protein, comprising the method as defined claim 1 and a step of detecting said isoform.

* * * * *